United States Patent
Burkett

(10) Patent No.: US 6,645,159 B1
(45) Date of Patent: Nov. 11, 2003

(54) WIRE JOINT AND METHOD

(75) Inventor: David H. Burkett, Temecula, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

(21) Appl. No.: 09/452,342

(22) Filed: Nov. 30, 1999

(51) Int. Cl.[7] .............................................. A61B 5/00
(52) U.S. Cl. ...................................................... 600/585
(58) Field of Search ................................ 604/525, 523, 604/524, 533, 921; 29/423; 600/585, 434, 433, 435, 462, 37

(56) References Cited

U.S. PATENT DOCUMENTS

| | | | |
|---|---|---|---|
| 4,827,941 A | 5/1989 | Taylor et al. ............... 128/657 |
| 4,846,193 A | 7/1989 | Tremulis et al. ............ 128/772 |
| 4,875,489 A | 10/1989 | Messner et al. ............ 128/772 |
| 4,966,163 A | 10/1990 | Kraus et al. ................ 128/772 |
| 5,135,503 A | 8/1992 | Abrams ....................... 604/164 |
| 5,188,621 A | 2/1993 | Samson ....................... 604/283 |
| 5,247,942 A | 9/1993 | Prather et al. .............. 127/772 |
| RE34,466 E | 12/1993 | Taylor et al. ................ 128/657 |
| 5,271,415 A | 12/1993 | Foerster et al. ............. 128/772 |
| 5,341,818 A | 8/1994 | Abrams et al. .............. 128/772 |
| 5,404,886 A | 4/1995 | Vance ......................... 128/772 |
| 5,415,178 A | 5/1995 | Hsi et al. .................... 128/772 |
| 5,511,559 A | 4/1996 | Vance ......................... 128/772 |
| 5,636,641 A | 6/1997 | Fariabi ........................ 128/772 |
| 5,637,089 A | 6/1997 | Abrams et al. .............. 604/95 |
| 5,676,659 A * | 10/1997 | McGurk ..................... 604/282 |
| 5,695,111 A | 12/1997 | Nanis et al. ................ 228/206 |
| 5,700,252 A * | 12/1997 | Klingenstein ............... 604/280 |
| 5,791,036 A * | 8/1998 | Goodin et al. .............. 29/423 |
| 5,813,996 A | 9/1998 | St. Germain et al. ....... 600/585 |
| 5,860,938 A | 1/1999 | Lafontaine et al. ......... 600/585 |
| 5,964,714 A | 10/1999 | Lafontaine .................. 600/561 |
| 5,980,471 A * | 11/1999 | Jafari ......................... 600/585 |
| 6,045,547 A * | 4/2000 | Ren et al. ................... 604/525 |
| 6,329,069 B1 * | 12/2001 | Azizi et al. ................. 428/600 |

* cited by examiner

Primary Examiner—Brian L. Casler
Assistant Examiner—Kevin C. Sirmons
(74) Attorney, Agent, or Firm—Fulwider Patton Lee & Utecht, LLP

(57) ABSTRACT

A process for joining two discrete wire components without the need of a third component, wherein material from the end of one wire component is removed to form a female end and the end of the other wire is formed into a male end. The male may be secured within the female end by conventional means. The female end may be formed by electrical discharge machining or laser drilling.

3 Claims, 2 Drawing Sheets

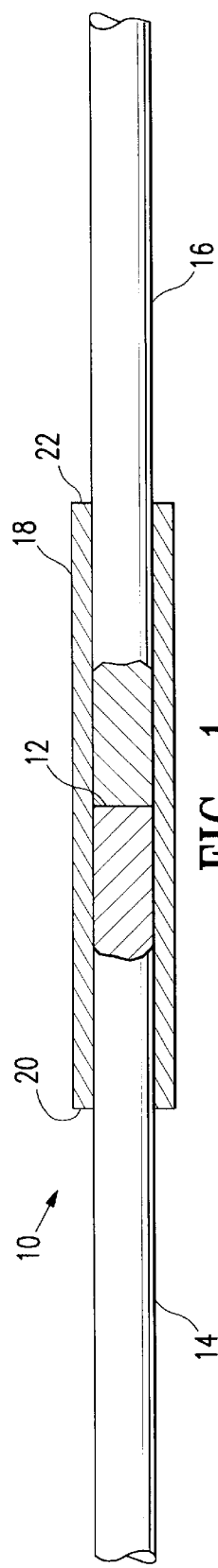
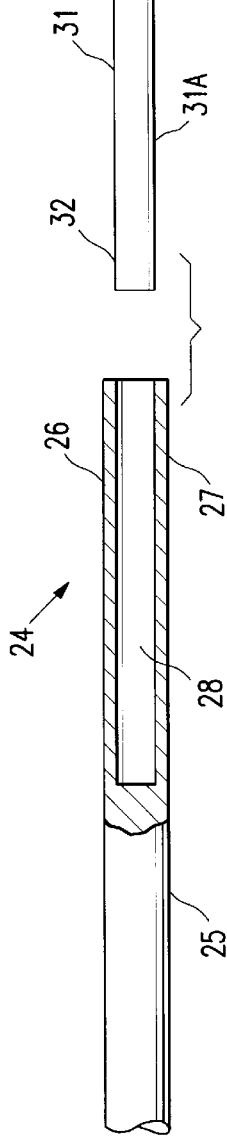
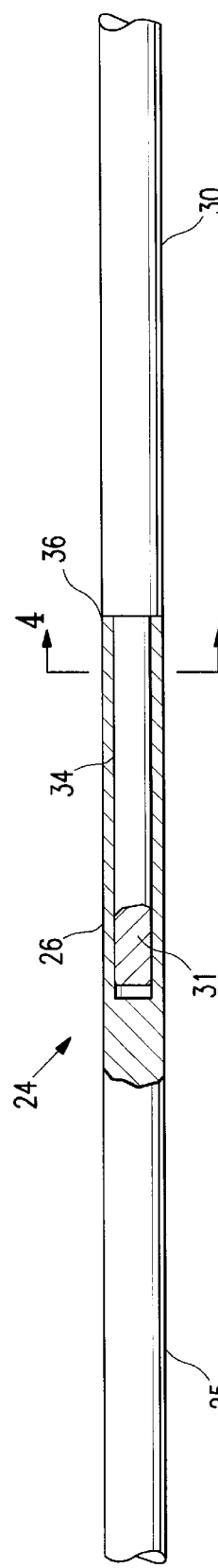
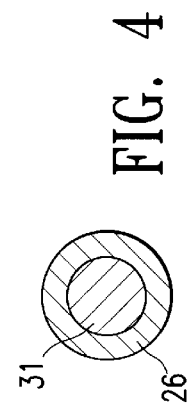

WIRE JOINT AND METHOD

BACKGROUND

Metallic wires are widely used in medical procedures, a common example being the guidewires used to locate intravascular devices such as angioplasty catheters. For various reasons, it is often desirable to join two discrete wire elements. For example, using different metal alloys can impart distinct handling characteristics to each wire element. By varying properties such as elasticity, strength and torqueability in each wire element, the overall handling of the guidewire can be varied or improved.

Conventional means for joining discrete wire elements involves the use of a third component, such as a hypotube. One end of each wire element is plunge ground and then inserted into the joining hypotube. The wire elements then can be secured to the hypotube, and thus to each other, by soldering or gluing. These prior art methods can be improved upon because the hypotube itself is expensive and increases manufacturing time due to the handling required to glue each wire element into the hypotube.

Accordingly, there is a need for improved wire joining processes that allow discrete wire elements to be joined without the use of a third element. There is also a need for wire joining processes that facilitate manufacturing and decrease costs. Additionally, it would be desirable to have a wire joining technique that produces a joint with a smooth continuous outer surface at the joint.

SUMMARY

The invention is directed to a process for forming a small diameter elongated device for use in a medical procedure, such as a guidewire, by joining a first elongated member to a second elongated member by forming a male end at an extremity formed of a first continuous material of the first elongated member, forming a female end at an extremity formed of a second continuous material of a second elongated member, inserting the male end into the female end, and permanently securing the male end to the female end. In one embodiment, formation of the female end is achieved by forming a hole by electrical discharge machining. In another embodiment, formation of the female end consists of forming a hole by laser drilling. Other focused energy methods are also suitable for forming the female end. Forming the male end can be carried out by mechanical abrasion, such as plunge grinding. Friction filting, crimping, soldering, gluing, brazing, laser welding, combinations thereof, or other suitable means may also be used to permanently secure the male end within the female end.

The invention is also directed to an elongated device for performing a medical procedure with a first elongated member having a male end at an extremity formed of a first continuous material permanently secured within a female end at an extremity of a second elongated member, the extremity of the second elongated member being formed of a second continuous material. The male and female ends being formable by the methods discussed above. In one embodiment, one elongated member is formed from stainless steel while the other elongated member is formed from a shape memory material such as Nitinol. In other embodiments, any suitable biocompatible material may be used for the elongate members or extremities thereof, including other metals, polymeric compositions or composites.

BRIEF DESCRIPTION OF THE DRAWINGS

FIG. 1 is an elevational view, partially in section, of a three component joint formed by conventional prior art methods.

FIG. 2 is an elevational view, partially in section, of an elongate member with a female end at an extremity and an elongate member with a male end at an extremity, embodying features of the invention.

FIG. 3 is an elevational view, partially in section, of the elongate members shown in FIG. 2 secured together and embodying features of the invention.

FIG. 4 is a cross sectional view of the elongate members shown in FIG. 3 taken along lines 4—4 in FIG. 3.

DETAILED DESCRIPTION

Figure 5:
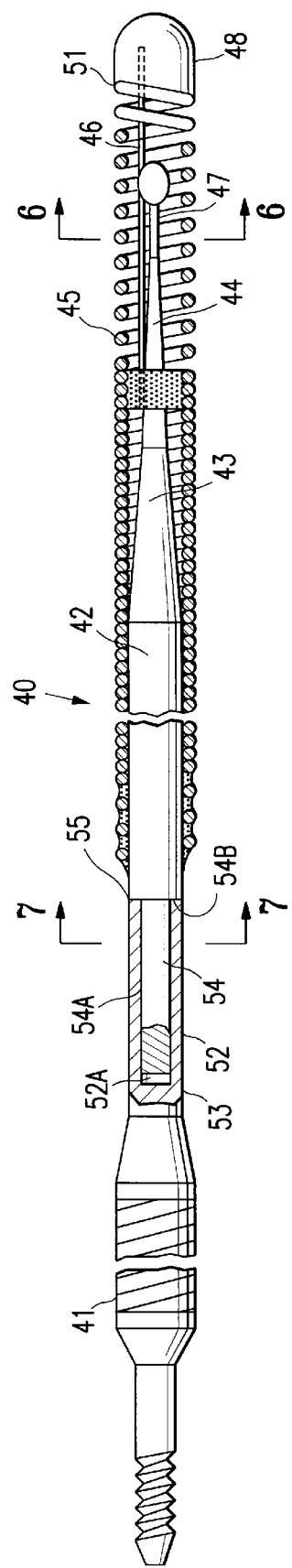
FIG. 5 is an elevational view in partial section of a guidewire having features of the invention.
Figure 6:
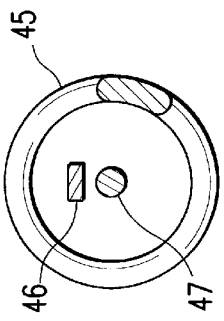
FIG. 6 is a transverse cross sectional view of the guidewire of FIG. 5 taken along lines 6—6 in FIG. 5.
Figure 7:
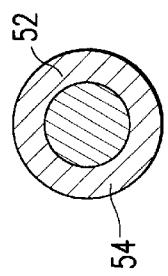
FIG. 7 is a transverse cross sectional view of the guidewire of FIG. 5 taken along lines 7—7 in FIG. 5.

FIG. 1 shows a portion of a guidewire 10 with wire joint 12 formed by conventional methods, having a first core wire 14 and a second core wire 16 coaxially disposed within hypotube 18. First and second core wires 14 and 16 are secured to hypotube 18 in a conventional manner, such as soldering, gluing or welding. The requirement of the hypotube to join the core wire segments necessitates two points of attachment. The hypotube joint creates two transition points 20 and 22 that are larger in diameter than the nominal diameter of the first and second core wires 14 and 16.

FIGS. 2–4 show a portion of a guidewire 24 joined by methods having features of the invention. Specifically, FIG. 2 shows a first core wire 25 having a female end 26 at an extremity 27. As shown in FIG. 2, extremity 27 of the first core wire 25 is formed of a continuous material which is a monogeneous structural extension of the first core wire 25 generally. The continuous material of the first core wire 25 extends to the extremity 27 and female end 26 without any additional components or materials. A hole 28 of the female end 26 can be formed by electrical discharge machining (EDM). Depending on the axial depth and diameter of hole 28, the cycle time for a hole EDM on a guidewire end will be about 10–30 sec. The hole 28 of the female end 26 may also be formed by other suitable focused energy removal means, such as laser drilling. The removal method should be operable with the precise tolerances required to form a small diameter hole in the wire. Second core wire 30 has a male end 31 configured to mate with hole 28 of female end 26. The male end 31 may be formed by removing material from the end of core wire 30 by any suitable means so as to produce a reduced diameter portion 31A. The reduced diameter portion 31A extends axially from a flanged portion 33. An abrasive operation such as plunge grinding may be used to form the male end 31. Other means of forming male end 31 include drawing the wire, pressing the wire, melting the wire and molding it or chemical removal of the wire material. Extremity 32 of second core wire 30 is formed of a continuous material which is a homogeneous structural extension of the second core wire 30 generally. The continuous material of the second core wire 30 extends axially to extremity 32 and male end 31 without any additional components or materials.

As shown in FIG. 3, and the cross section of, FIG. 4, male end 31 fits closely within female end 26 and the two ends may be secured by soldering, gluing, welding, brazing and the like, to form wire joint 34. Alternatively, male end 31 and female end 26 may be configured so that press fitting them generates sufficient friction to secure them together. It is also possible for the joint 34 to be swaged or crimped to secure the wire cores 26 and 30 at joint 34. Regardless of the method of attachment, it is important to allow the transmission of torque through the joint 34 to maintain steerability of the guidewire 24. Joining core wires 26 and 30 as shown in FIG. 3 and discussed above requires only one point of attachment and creates only one effective transition point 36. These features improve the reliability of guidewire 24 by creating fewer failure points and improving the crossing characteristics by creating a joint 34 with a smooth continuous outer surface at the transition point 36.

The joining methods of the invention can allow a guidewire 40, shown in FIG. 5, to be formed with two adjacent components joined together to impart different handling characteristics to each section. In the embodiment shown in FIG. 5, an elongated proximal core portion 41 or a proximal section 41 is formed from stainless steel while a distal core portion 42 or a distal section 42 is formed from a nickel-titanium allow having pseudo-elastic or super-elastic characteristics, such as NiTi, commonly called NITI-NOL. Other metals having super- or pseudo-elastic properties may also be desirable. The invention is not limited to metals as other suitable bio-compatible materials such as polymers or composites may be used.

The proximal section 41 of the guidewire 40 is generally about 130 to about 140 cm in length with an outer diameter of about 0.006 to about 0.018 inch for coronary use. The distal section 42 can have nominal transverse dimensions similar to those of proximal section 41, however, the distal section 42 typically has one or more tapered distal portions 43 and 44 which taper distally to a reduced diameter or transverse dimension. Larger diameter guidewires up to about 0.038 inch may be employed in peripheral arteries and other body lumens. Guidewire 40 may also have a flexible body member such as a helical coil 45 disposed about the distal section 42. A shapable member 46, which may be the distal extremity of the distal section 42, or a separate shaping ribbon 46, as shown in FIG. 5, is secured to the distal end 47 of the distal section 42. The distal section 42 extends through the helical coil 45 and is secured to a rounded plug 48 at a distal end 51 of the helical coil 45. The lengths of the tapered distal portions 43 and 44 can range from about 2 to about 20 cm, depending upon the stiffness or flexibility desired in the final product. The helical coil 45 is about 20 to about 45 cm in length, has an outer diameter about the same size as the diameter of the proximal section 41, and is made from wire about 0.002 to 0.003 inch in diameter. The shapable member 46 can have a ribbon with a rectangular transverse cross-section, usually having dimensions of about 0.001 by 0.003 inch.

The proximal section 41 has a female end 52 with a hole 52A disposed at a distal extremity or end 53 of the proximal section 41. A male end 54 with a reduced diameter portion 54A extending proximally from a flanged portion 54B is disposed at a proximal extremity or end 55 of distal section 42. The female end 52 and male end 54 can be engaged and secured in a similar fashion to the female end 28 and the male end 32 of the embodiment shown in FIG. 3. The reduced diameter portion 54A of the male end 54 can have a length of about 0.005 to about 0.20 inch, specifically about 0.02 to about 0.06 inch. The depth of hole 52A of the female end 52 should be comparable to the length of the reduced diameter portion 54A of the male end 54.

Described herein are preferred embodiments, however, one skilled in the art that pertains to the present invention will understand that there are equivalent alternative embodiments. Although the described embodiments have comprised guidewires, the invention can be used to create other solid, elongated, small diameter medical devices from two or more discrete sections. For example, devices such as pacing leads may be formed using the methods disclosed herein.

What is claimed is:

1. A guidewire comprising an elongated proximal core portion having a female end disposed at a distal extremity of the proximal core portion formed from a first continuous material; a distal core portion having a male end disposed at a proximal extremity of distal core portion, with the male end permanently secured within the female end; a flexible body member disposed about and secured to the distal core portion; and a shapable member secured to the distal core portion and extending through the flexible body member.

2. A guidewire comprising an elongated proximal core portion having a male end disposed at a distal extremity of the proximal core portion formed from a first continuous material including stainless steel; a distal core portion having a female end with a predetermined depth disposed at a proximal extremity formed from a second continuous material including a nickel-titanium alloy, with the male end permanently secured within the female end; and a flexible body member disposed about and secured to the distal core portion.

3. A guidewire comprising a proximal section having an outer diameter smaller than 0.04 inch, and having a female end of a predetermined depth disposed at a distal end of the proximal section; and a distal section having an outer diameter smaller than 0.04 inch, and having a male end disposed at a proximal end of the distal section, with the male end permanently secured within the female end such that the guidewire forms a joint having an outer diameter that is substantially the same as the outer diameter of the female end, wherein the joint has a smooth, continuous outer surface at a transition point.

* * * * *